(12) United States Patent
Otsubo

(10) Patent No.: US 6,645,186 B2
(45) Date of Patent: Nov. 11, 2003

(54) DISPOSABLE BODY FLUID ABSORBENT WEARING ARTICLE

(75) Inventor: Toshifumi Otsubo, Kagawa-Ken (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/026,725

(22) Filed: Dec. 27, 2001

(65) Prior Publication Data

US 2002/0087140 A1 Jul. 4, 2002

(30) Foreign Application Priority Data

Dec. 28, 2000 (JP) ........................................ 2000-401007

(51) Int. Cl.[7] ............................................... A61F 13/15
(52) U.S. Cl. .................................................. 604/385.01
(58) Field of Search ....................... 604/385.01, 385.19, 604/385.24, 385.26

(56) References Cited

U.S. PATENT DOCUMENTS

| 5,382,246 A | * | 1/1995 | Kawano | 604/385.24 |
|---|---|---|---|---|
| 5,558,660 A | * | 9/1996 | Dreier | 604/385.19 |
| 5,575,785 A | * | 11/1996 | Gryskiewicz et al. | 604/385.28 |
| 5,601,544 A | * | 2/1997 | Glaug et al. | 604/385.28 |
| 6,152,908 A | * | 11/2000 | Widlund et al. | 604/385.19 |
| 6,159,191 A | * | 12/2000 | Mishima et al. | 604/385.28 |
| 2002/0029029 A1 | * | 3/2002 | Otsubo | 604/385.101 |
| 2003/0004483 A1 | * | 1/2003 | Otsubo | 604/385.01 |

FOREIGN PATENT DOCUMENTS

| JP | 7-11203 | 5/1995 |
|---|---|---|
| JP | 7-155344 | 6/1995 |

* cited by examiner

Primary Examiner—Weilun Lo
Assistant Examiner—Michael G. Bogart
(74) Attorney, Agent, or Firm—Lowe Hauptman Gilman & Berner LLP

(57) ABSTRACT

A disposable body fluid absorbent wearing article includes a body fluid absorbent pad, and a crotch region of the pad is defined by a pair of darts extending in a back-and-forth direction of the article. The article has a body fluid absorbent core divided into an inner portion extending between the darts and outer portions respectively extending outside the respective darts.

15 Claims, 8 Drawing Sheets

DISPOSABLE BODY FLUID ABSORBENT WEARING ARTICLE

BACKGROUND OF THE INVENTION

This invention relates to disposable body fluid absorbent wearing articles including disposable diapers as a specific embodiment.

Japanese Patent Application Publication No. 1995-112003A discloses a disposable absorbent pad basically comprising a pad itself and a waist-band. More specifically, this absorbent pad comprises a liquid-pervious topsheet, a liquid-impervious backsheet and a liquid-absorbent core disposed between these two sheets. The waist-band is connected to longitudinal ends of respective end flaps extending outward from longitudinally opposite end regions of the core. The absorbent pad has a pair of side flaps transversely extending the pad and being stretchable in a longitudinal direction thereof and these side flaps are at least partially folded in the longitudinal direction back onto an inner surface of the absorbent pad. The pad itself comes in close contact with inner sides of the wearer's thighs as this absorbent pad is worn with the elastic waist-band pressed against the wearer's waist.

Japanese Patent Application Publication No. 1995-155344A discloses disposable pants basically comprising an elastic pants member and a pad member. More specifically, the pad member comprises a liquid-pervious topsheet, a liquid-impervious backsheet and a liquid-absorbent core disposed between these two sheets wherein a pair of end flaps and a pair of side flaps extending outward from longitudinally opposite end regions and transversely opposite side edge regions of the core, respectively. Longitudinal ends of the respective end flaps are fixed to the pants member in the vicinity of its waist-line. The side flaps are longitudinally stretchable and define pockets opening inwardly of the pad member. The pad member comes in close contact with inner sides of the wearer's thighs as the pants member is worn.

The body fluid absorbent pads such as the pad itself and the pad member as disclosed in the above-cited Japanese Patent Application Publication Nos. 1995-112003A and 1995-155344A, respectively, intend to bring them in close contact with the inner sides of the wearer's thighs. To achieve this, a width of the pad in its crotch region is strictly limited, so surface area as well as volume of the pad used to absorb body fluids is strictly limited and it is sometimes difficult for these absorbent pads of prior art to absorb body fluids rapidly.

SUMMARY OF THE INVENTION

It is an object of this invention to provide an improved disposable body fluid absorbent wearing article so that body fluids can be rapidly absorbed in spite of a restricted width of the body fluid absorbent pad in its crotch region.

According to this invention, there is provided a disposable body fluid absorbent wearing article comprising a body fluid absorbent pad which includes a body fluid absorbent core and a liquid-pervious topsheet covering an upper surface of the core, the pad having a front waist region, a rear waist region and a crotch region extending between these waist regions wherein at least the front and rear waist regions of the three regions are integral with means used to put the article on a wearer's body.

The pad is provided along its transversely opposite sides in its crotch region with a pair of transversely opposite darts formed by partially joining at least the topsheet. The pad is composed, in its transverse direction, of an inner core lying between the pair of darts, and outer cores lying outside the respective darts, constituting together the core. The core has its outer periphery surrounded by end and side flaps formed by at least the topsheet.

In one preferred embodiment of this invention, the pair of darts may curve toward a center line bisecting a width of the pad and delineate circular arcs, and the side flaps extending outward beyond transversely opposite side edges of the core are folded back toward the inner surface of the pad and joined at front and rear end portions of the side flaps to the inner surface so that a pair of pockets opening inwardly of the pad may be formed between the side flaps and the outer cores, respectively, and the side flaps are provided along the folded inner side edge portions with elastic members joined under extension thereto in parallel to the center line.

DETAILED DESCRIPTION OF THE PREFERRED EMBODIMENTS

Details of a body fluid absorbent wearing article according to this invention will be more fully understood from the description of a disposable diaper as the typical embodiment given hereunder with reference to the accompanying drawings.

Figure 1:
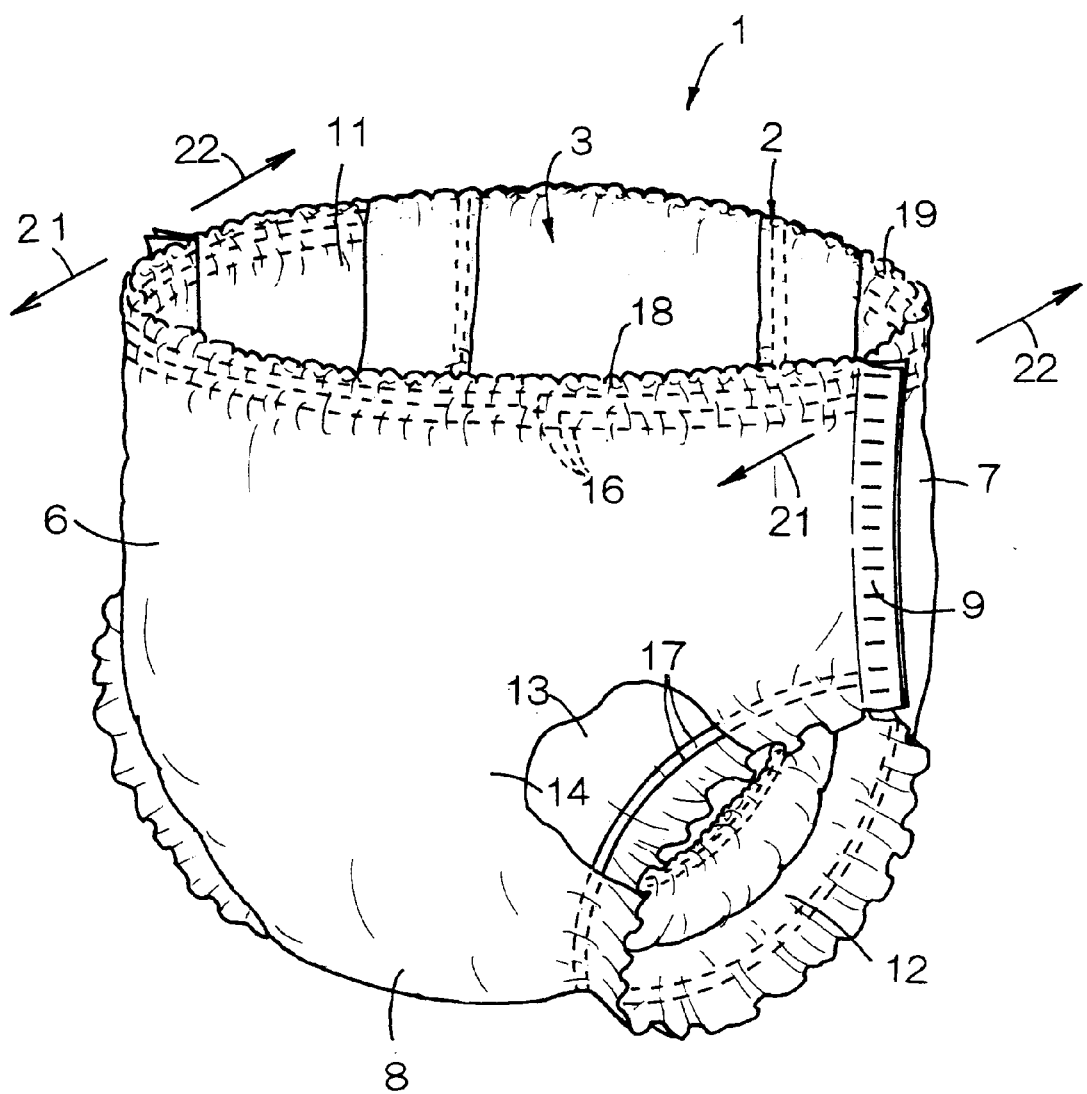
FIG. 1 is a partially cutaway perspective view showing a wearing article.

A disposable diaper 1 shown by FIG. 1 in a partially cutaway perspective view has a pants-type cover 2 and a body fluid absorbent pad 3 attached to an inner side of the cover 2. The cover 2 is composed of a front waist region 6, a rear waist region 7 and a crotch region 8. The front and rear waist regions 6, 7 are joined together at welding zones 9 provided along transversely opposite side edge portions of the respective waist regions so as to form a waist-hole 11 and a pair of leg-holes 12. The cover 2 is formed of a laminated sheet of liquid-impervious plastic film 13 and a nonwoven fabric 14 and, along peripheral edge portions of the waist-hole 11 and the leg-holes 12, elastic members 16, 17 extend between the film 13 and the nonwoven fabric 14 and joined under extension to inner surface(s) of the film 13 and/or the nonwoven fabric 14. The pad 3 extends on the inner surface of the cover 2 across the crotch region 8 to waist-hole's edge portions 18, 19 of the front and rear waist regions 6, 7, respectively.

Figure 2:
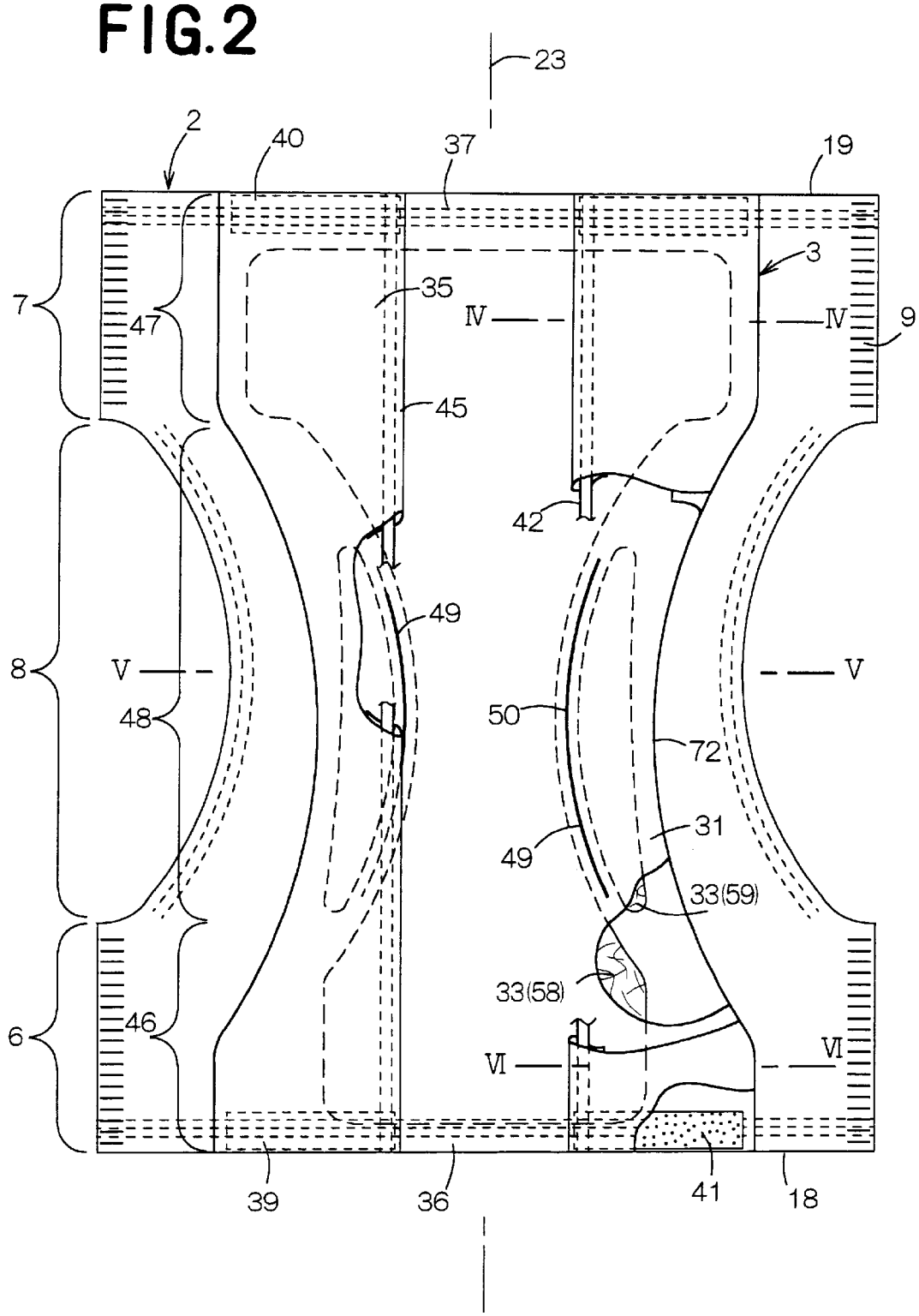
FIG. 2 is a partially cutaway plan view showing a wearing article as unfolded.

FIG. 2 is a partially cutaway plan view showing the diaper 1 as unfolded in directions indicated by arrows 21, 22 in FIG. 1 so as to separate the front and rear waist regions from each other along the welding zones 9 of the cover 2 and partially cutaway. The cover 2 unfolded in this manner presents an hourglass-shape, i.e., the transversely opposite side edge portions in the crotch region 8 curve inward to delineate circular arcs. The pad 3 extending between the longitudinally opposite end portions 18, 19 of the cover 2 lies on a longitudinal center line 23 bisecting a width of the cover 2.

The pad 3 comprises a liquid-pervious topsheet 31 facing the wearer of the diaper 1, a liquid-impervious backsheet 32 facing the cover 2 and a liquid-absorbent core member 33 disposed between these two sheets 31, 32. Similar to the cover 2, the pad 3 is composed of front and rear waist regions 46, 47, and a crotch region 48 extending between these two waist regions 46, 47. Between the longitudinally opposite end portions 18, 19 defining the waist-hole, the respective regions 46–48 have dimensions substantially matching those of the regions 6–8 of the cover 2. The top- and backsheets 31, 32 extend outward beyond a peripheral edge of the core 33 and are water-tightly joined to each other to form a pair of end flaps 36, 37 and a pair of side flaps 35, 35 surrounding the outer periphery of the core 33. The end flaps 36, 37 are joined to inner surfaces of the longitudinally opposite end portions 18, 19 of the cover 2 by means of adhesive 55 (See FIG. 3) and the side flaps 35 are folded back toward the inner surface of the pad 3. Front and rear end portions 39, 40 of the side flaps 35 are joined to the inner surface of the pad 3 by means of hot melt adhesive 41 so that respective intermediate portions defined between the front and rear end portions 39, 40 are kept not joined to the inner surface of the pad 3. Inner side edge portions 45 of the respective side flaps 35 are folded back so as to form tubular spaces extending in parallel to the center line 23 and to wrap elastic members 42 joined under extension to inner surfaces of these tubular spaces. The crotch region 48 of the pad 3 is provided on both sides of the center line 23 with a pair of opposite darts 49, respectively, curving toward the center line 23 so as to delineate circular arcs.

Figure 3:
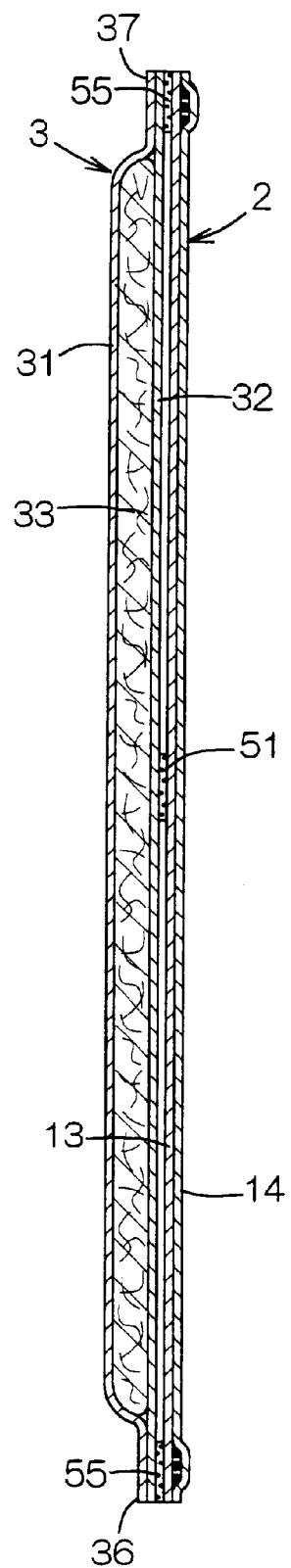
FIG. 3 is a cross-sectional view taken along a center line in FIG. 2.

FIG. 3 is a cross-sectional view taken along the center line 23 in FIG. 2. The cover 2 comprises the film 13 and the nonwoven fabric 14 intermittently joined to each other using adhesive or welding (not shown). In the pad 3, the top- and backsheets 31, 32 extend outward beyond the longitudinally opposite ends of the core 33 to form the end flaps 36, 37. Not only the front and rear end flaps 36, 37 of the pad 3 are joined to the cover 2 by means of adhesive 55 but the zone lying on the center line 23 and other appropriate zones also are joined to the cover 2 by means of adhesive 51.

Figure 4:
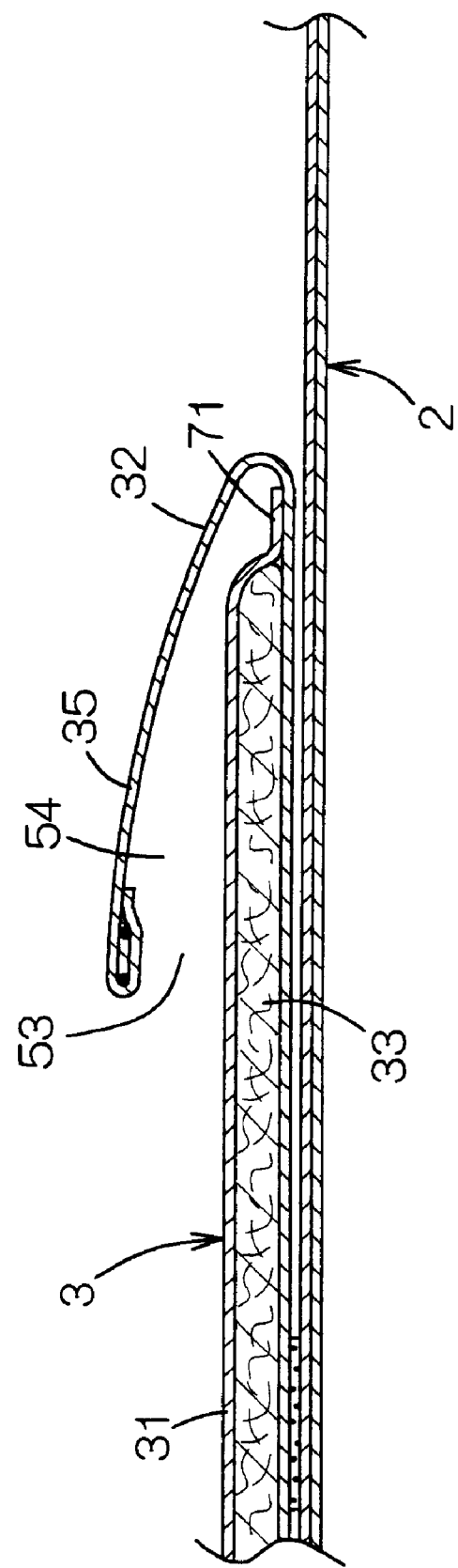
FIG. 4 is a cross-sectional view taken along a line IV—IV in FIG. 2.
Figure 5:
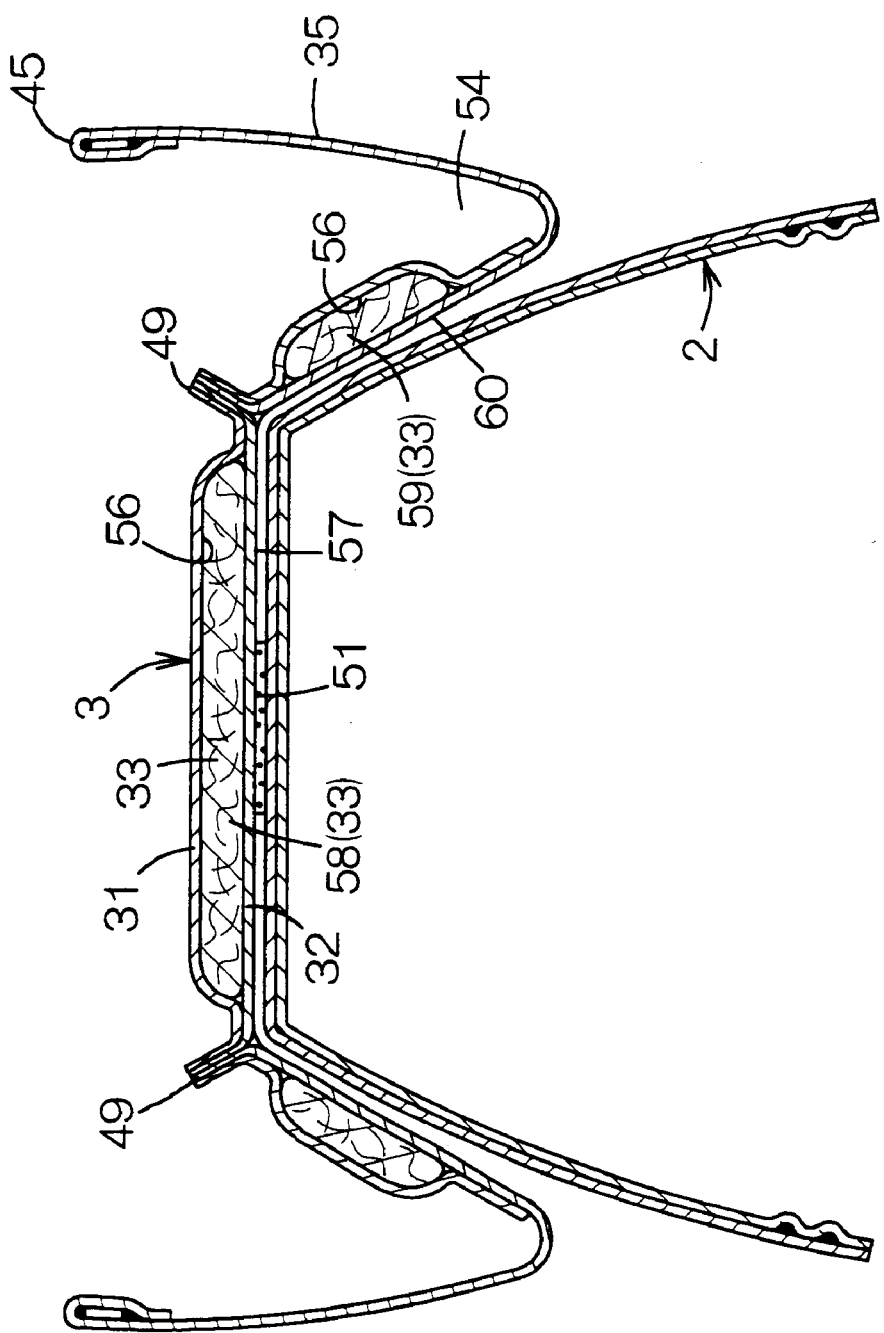
FIG. 5 is a cross-sectional view taken along a line V—V in FIG. 2.
Figure 6:
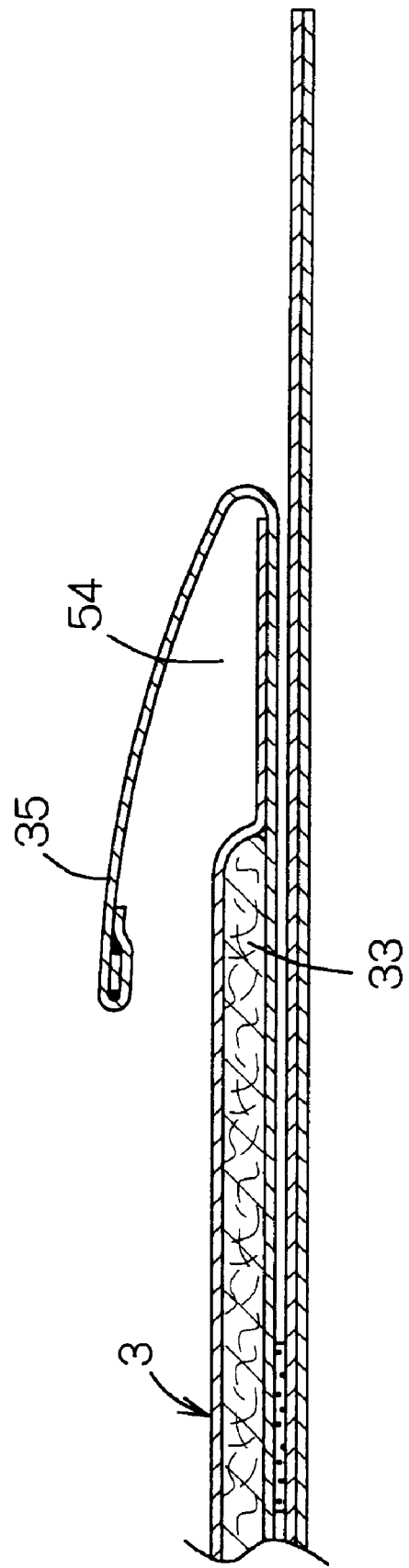
FIG. 6 is a cross-sectional view taken along a line VI—VI in FIG. 2.

FIGS. 4–6 are cross-sectional views taken along lines IV—IV, V—V and VI—VI, respectively, in FIG. 2. The line V—V matches a transverse center line bisecting the pad 3 into upper and lower halves. Referring to FIG. 4, the top- and backsheets 31, 32 of the pad 3 extend outward beyond the core 33 and are overlaid and joined together. The backsheet 32 extends outward further beyond the topsheet 31 so as to form most of the side flaps 35. Such side flaps 35 are folded back inwardly of the pad 3 so as to cover the core 33 and thereby to form pockets 54 respectively having openings 53 oriented inward.

Referring to FIG. 5, the top- and backsheets 31, 32 cover an inner core 58 defined between the darts 49, 49 and cover an outer cores 59 defined outside the respective darts 49, 49. The respective darts 49 are formed by overlaying opposite side edge portions of the lower surfaces 56 of each pair of the adjacent topsheets 31 covering the inner core 58 and the adjacent outer core 59, respectively, together and overlaying the respective inner side edge portions of the lower surfaces 57 of each pair of the adjacent backsheets 32 covering the inner core 58 and the adjacent outer cores 59 together and bonding them using appropriate welding technique or adhesive. The inner core 58 and the outer cores 59 constituting the core 33 are separated by the respective darts 49 one from another in the transverse direction (See FIG. 2). The top- and backsheets 31, 32 covering the respective outer cores 59 extend outward beyond outer side edges of the respective outer cores 59 forming a part of the side edge portions of the core 33 and joined to each other. The backsheet 32 extends further outward beyond the side edges of the topsheet 31 and forms most of the side flaps 35. In the crotch region 48 of such pad 3, with respect to the inner core 58 horizontally extending as shown, side edge portions 60 of the pad 3 inclusive of the outer cores 59 tend to pivotally hang down obliquely from the inner core 58 around the darts 49 each having a put flat structure and functioning as a hinge. In this state, the side flaps 35 are folded back upward in the vicinity of the outer side edges of the respective outer cores 59 and the pockets 54 also extend obliquely upward. The darts 49 functioning in this manner are obtained by drawing the side edge portions of the top- and backsheets 31, 32 toward the center line 23 in the crotch region 48 of the pad 3 so that these side edge portions form circular arcs as seen in FIG. 2 and bonding the top- and backsheets 31, 32 along these circular arcs. The darts 49 in a shape of such circular arcs have the apices 50 adjacent the center line 23. The inner side edge portions 45 of the side flaps 35 are preferably placed above the vicinity of the respective apices so that the pockets 54 may be formed between the side flaps 35 and the outer cores 59, respectively. In the pad 3, formation of the darts 49 causes fold lines 72 of the side flaps 35 to curve inwardly of the pad 3, delineating circular arcs.

Referring to FIG. 6, the side flaps 35 form the pockets 54 as in the case of FIG. 4. It should be understood that the core 33 is narrower in the front waist region 46 than in the rear waist region 47 of the pad 3 and the core 33 does not extend to the innermost regions of the pockets 54. While it is possible to increase the width of the core 33 in the front waist region 46 to be relatively large as in the rear waist region 47, it is preferred to restrict the width of the core 33 in the front waist region 46 as shown in FIG. 2 so that bulkiness possibly occurring in the front waist region 46 can be alleviated.

Figure 7:
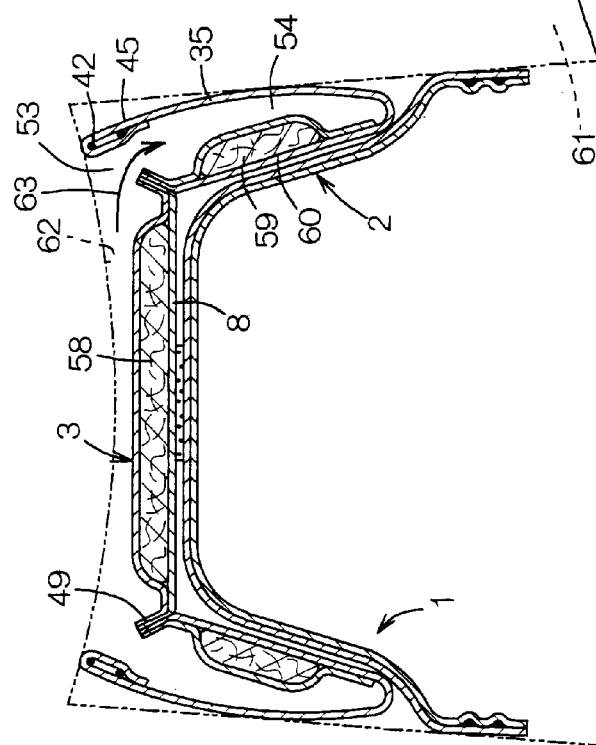
FIG. 7 is a cross-sectional view of the wearing article as it is worn.

FIG. 7 is a schematic view showing the diaper 1 put on the wearer's body with the crotch region 48 of the pad 3 bearing against the wearer's skin. The inner core 58 defined between the darts 49, 49 is placed against a zone 62 defined between groins of the wearer's thighs 61 indicated by imaginary lines. The darts 49 extend toward the groins of the thighs 61 and function like hinges around which the side edge portions 60 of the pad 3 inclusive of the outer cores 59 pivotally hang down along the inner sides of the thighs 61. With the diaper 1 curving about the crotch region 8 toward the front and rear waist regions 6, 7, in a U-shape along the wearer's body, contraction of the elastic members 42 causes the side flaps 35 to rise on the pad 3 and the inner side edge portions 45 of the side flaps 35 bear against the vicinity of the groins of the thighs 65 from below. The side flaps 35 cooperate with the outer cores 59 to form the pockets 54 having the openings 53, respectively. With the diaper 1 in this state, the inner core 58 is dimensioned to be sufficiently narrow to be received in the space defined between the groins of the thighs 61 without formation of many wrinkles and consequently it may be difficult for the inner core 58 alone to absorb body fluids quickly. However, such limited absorbing capacity of the inner core 58 is effectively compensated by the outer cores 59. Specifically, an excessive amount of body fluids flowing into the respective pockets 54 as indicated by an arrow is not only prevented from leaking from the diaper 1 but also absorbed by the outer cores 59.

Figure 8:
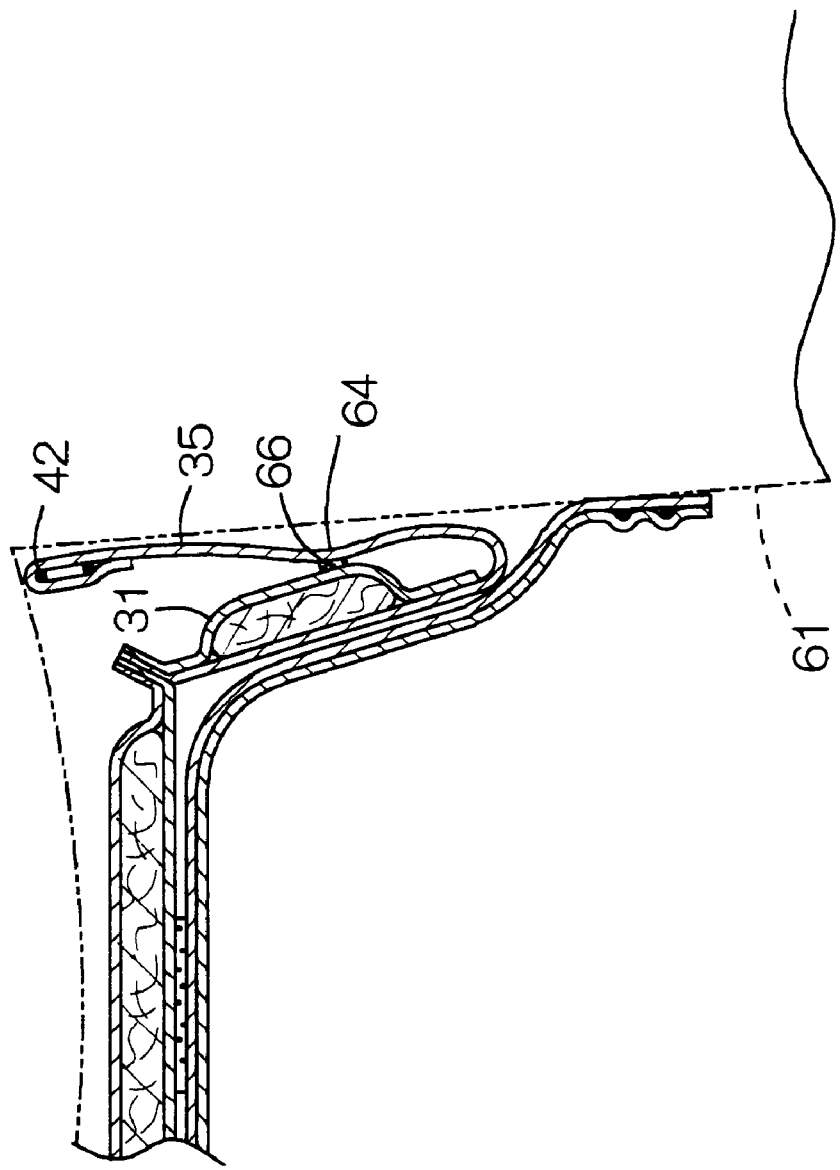
FIG. 8 is a view similar to FIG. 7 of another preferred embodiment of this invention.

FIG. 8 is a view similar to FIG. 7 showing an alternative embodiment of this invention, in which the diaper 1 is shown partially cutaway. With the diaper 1 according to this embodiment, in the vicinity of a center line V—V bisecting a longitudinal dimension of the pad 3, the side flaps 35 are locally bonded, in zones 64 on the inner surfaces thereof, to the topsheet 31 covering the outer cores 59 by means of adhesive 66 so that the portions of these flaps 35 extending above the zones 64 may be held substantially upright. In the case of the embodiment shown in FIG. 7, it is apprehended, depending on how the diaper 1 is put on the wearer's body, that the portions of the side flaps 35 extending downward from the elastic members 42 might slacken to reduce the effective volume of the respective pockets 54 and to prevent body fluids from smoothly flowing into the pockets 54. Such apprehension can be avoided by keeping the portions of the side flaps 35 defined between the elastic members 42 and the zones 64, respectively, substantially upright.

According to this invention, the means to hold the pad 3 against the wearer's body is not limited to the pants-type cover 2 as shown. For example, it is possible without departing from the scope of this invention to attach the front and rear end portions 36, 37 of the pad 3 to a belt-like member adapted to be draped around the wearer's torso. In the case of the pants-type cover 2, the pants as a whole may be formed using either a liquid-pervious sheet or a liquid-impervious sheet. The side flaps 35 of the pad 3 are illustrated to have the proximal end portions 71 (See FIG. 4) formed by the top- and backsheets 31, 32 and the remaining portions formed by the backsheet 32 alone. However, it is possible without departing from the scope of this invention to form the side flaps 35 by separately prepared sheets joined to the topsheet 31 or the backsheet 32. In any way, the side flaps 35 are preferably liquid-impervious.

The disposable body fluid absorbent wearing article according to this invention is primarily characterized in the arrangement such that the inner portion of the body fluid absorbent pad is formed along its transversely opposite side edges with the darts from the outer sides of which the pad hangs down to form the respective outer portions of the pad substantially along the wearer's thighs so that these outer portions cooperate with the side flaps to form the pockets opening inwardly of the pad. Such unique arrangement allows the wearing article to absorb body fluids reliably and quickly even though the width of the pad is dimensioned to be so narrow that the pad can be tightly placed against the wearer's skin between the groins of the thighs without formation of many wrinkles.

What is claimed is:

1. A disposable body fluid absorbent garment, comprising:
    a body fluid absorbent pad which includes at least a body fluid absorbent core and a liquid-pervious topsheet covering an upper surface of said absorbent core, said pad having a front waist region, a rear waist region and a crotch region extending between said front and rear waist regions; and
    means for holding said absorbent pad to face a wearer's body when said garment is worn by the wearer;
    wherein
    said absorbent pad is provided along transversely opposite sides thereof, in said crotch region, with a pair of transversely opposite darts formed by at least said topsheet;
    said absorbent core comprises an inner absorbent core lying between said pair of darts and lateral outer absorbent cores lying outside the respective darts and
    said absorbent core having an outer periphery surrounded by end and side flaps formed by at least said topsheet.

2. The garment according to claim 1, wherein said darts are curved toward a center line bisecting a width of said absorbent pad and delineate circular arcs.

3. The garment according to claim 1, wherein
    said side flaps, which extend outward beyond transversely opposite side edges of said absorbent core, are folded back toward an upper surface of said absorbent pad and joined at front and rear longitudinal end portions of said side flaps to said upper surface so that a pair of pockets opening inwardly of said absorbent pad are formed between said side flaps and said outer absorbent cores, respectively; and
    said side flaps are provided along folded inner side edge portions thereof with elastic members secured under extension to said folded inner side edge portions.

4. The garment according to claim 3, wherein said inner side edge portions of said side flaps, in a folded back state, are positioned in the vicinity of apices of the darts.

5. The garment according to claim 3, wherein intermediate zones between said front and rear end portions of said side flaps are joined to upper surfaces of said outer absorbent cores.

6. The garment according to claim 1, wherein said means include a pants-type cover.

7. A body fluid absorbent pad, having a front waist region, a rear waist region and a crotch region extending between said front and rear waist regions, said body fluid absorbent pad comprising:
    a central absorbent core braced by lateral outer absorbent cores positioned on opposite lateral sides of said central core; and
    darts each located between the central core and one of the outer cores;
    wherein said darts extend along two lines extending longitudinally along transversely opposite sides of said central core, said lines being spaced apart from each other by a distance gradually increasing from a minimum at a longitudinally middle point thereof to a maximum at longitudinally opposite ends thereof.

8. The body fluid absorbent pad of claim 7, further comprising a liquid-pervious topsheet covering upper surfaces of said central and outer cores, wherein said darts are formed at least by said topsheet.

9. The body fluid absorbent pad of claim 7, wherein each of said central and outer cores are individually wrapped by a topsheet and a backsheet, and each of said darts is formed by the topsheets and backsheets of the central core and one of the outer cores.

10. A body fluid absorbent pad, having a front waist region, a rear waist region and a crotch region extending between said front and rear waist regions, said body fluid absorbent pad comprising:
    a central absorbent core braced by lateral outer absorbent cores positioned on opposite lateral sides of said central core;
    darts each located between the central core and one of the outer cores; and side flaps which extend outward beyond lateral outer side edges of the outer cores and are foldable back to an upper surface of said body fluid absorbent pad, said side flaps being joined at front and rear longitudinal end portions thereof to said upper surface so as to form a pair of side pockets between said side flaps and the respective outer cores.

11. The body fluid absorbent pad of claim 10, further comprising a liquid-pervious topsheet covering upper surfaces of said central and outer cores, wherein said darts are formed at least by said topsheet.

12. The body fluid absorbent pad of claim 11, wherein said side flaps are provided along inner side edge portions thereof with elastic members secured under extension thereto.

13. The body fluid absorbent pad of claim 11, wherein said inner side edge portions of said side flaps, in a folded back state, are positioned in the vicinity of apices of the darts.

14. The body fluid absorbent pad of claim 11, wherein a middle portion between the front and rear end portions of each of said side flaps is joined to the upper surface of the respective outer core.

15. The body fluid absorbent pad of claim 10, wherein each of said central and outer cores are individually wrapped by a topsheet and a backsheet, and each of said darts is formed by the topsheets and backsheets of the central core and one of the outer cores.

* * * * *